(12) United States Patent
Santhanagopalan et al.

(10) Patent No.: US 10,107,696 B2
(45) Date of Patent: Oct. 23, 2018

(54) METHODS AND DEVICES FOR ELECTROCHEMICAL SYSTEM ANALYSIS

(71) Applicant: Alliance for Sustainable Energy, LLC, Golden, CO (US)

(72) Inventors: Shriram Santhanagopalan, Lakewood, CO (US); Matthew Allen Keyser, Arvada, CO (US); Aron Ray Saxon, Golden, CO (US); John Ireland, Sunnyvale, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 366 days.

(21) Appl. No.: 14/855,538

(22) Filed: Sep. 16, 2015

(65) Prior Publication Data

US 2017/0074731 A1    Mar. 16, 2017

(51) Int. Cl.
*G01K 17/00*     (2006.01)
*G01N 25/20*     (2006.01)
*H01M 10/42*     (2006.01)

(52) U.S. Cl.
CPC .............. *G01K 17/00* (2013.01); *G01N 25/20* (2013.01); *H01M 10/4285* (2013.01)

(58) Field of Classification Search
CPC ...................................................... G01K 17/00
See application file for complete search history.

(56) References Cited

U.S. PATENT DOCUMENTS 3,733,887 A  *  5/1973  Stanley ................. G01N 25/18
                                                          374/44

4,126,032 A     11/1978  Ikeda et al.
(Continued)

FOREIGN PATENT DOCUMENTS

EP          1 924 849         10/2007
WO    WO 2010/105062 A1        9/2010

OTHER PUBLICATIONS

Dandeville ("Analyse thermique et électrochimique de supercondensateurs carbone-MnO2 en milieu aqueux". Génie des procédés. Université de Nantes, 2012. Français. <tel-00765136>, pp. 51-81).*

(Continued)

*Primary Examiner* — Clayton E Laballe
*Assistant Examiner* — Leon W Rhodes, Jr.
(74) *Attorney, Agent, or Firm* — Robert G. Pittelkow; Alexandra M. Hall

(57) ABSTRACT

The present disclosure provides a calorimeter device and an electrochemical system analysis method. The device includes a first thermo-electric gauge (TEG) and a first conductor thermally coupled to the first TEG, the first conductor comprising a first surface. The device may also include a second conductor with a second surface, the second surface facing the first surface, thereby forming a gap. The device may also include a second TEG thermally coupled to the second conductor and an adjustment mechanism attached to the second TEG, operable to modify a size of the gap between the first surface and the second surface. The method includes applying a plurality of electrical signals across an electrochemical system, determining, using a calorimeter, at least one rate at which heat is generated by the system, and determining at least one thermal characteristic of a component of the system.

9 Claims, 8 Drawing Sheets

(56) References Cited

U.S. PATENT DOCUMENTS

| | | | |
|---|---|---|---|
| 4,416,551 | A | 11/1983 | Kim |
| 6,016,047 | A | 1/2000 | Notten et al. |
| 6,079,873 | A | 6/2000 | Cavicchi et al. |
| 6,137,269 | A | 10/2000 | Champlin |
| 6,833,707 | B1 * | 12/2004 | Dahn ................ G01N 25/4846 324/426 |
| 8,613,545 | B2 | 12/2013 | Herrera Gómez et al. |
| 2012/0182025 | A1 | 7/2012 | Maxey et al. |
| 2012/0250723 | A1 | 10/2012 | Blumm |
| 2014/0003460 | A1 | 1/2014 | Keyser et al. |

OTHER PUBLICATIONS

Pascot et al ("Calorimetric measurement of the heat generated by a Double-Layer Capacitor cell under cycling." Thermochimica Acta, vol. 510, No. 1-2, 2010, pp. 53-60., doi:10.1016/j.tca.2010.06.022.).*

Xiao et al ("Theoretical and experimental analysis of heat generations of a pouch type LiMn2O4/Carbon high power Li-Polymer battery." Journal of Power Sources, vol. 241, 2013, pp. 46-55., doi:10.1016/j.jpowsour.2013.04.062.).*

Author Unknown, "The THT Micro Reaction Calorimeter µRC", Chemical Applications Brochure, http://www.thermalhazardtechnology.com/uploaded_images/files/144_uRCApplicaitonsBrochure.pdf, accessed 2015, pp. 1-6.

Eddahech et al., "Thermal Characterization of a High-power Lithium-ion Battery: Potentiometric and Calorimetric Measurement of Entropy Changes", Energy, 2013, vol. 61, pp. 432-439.

Fleckenstein et al., "Thermal Impedance Spectroscopy—A Method for the Thermal Characterization of High Power Battery Cells", Journal of Power Sources, 2013, vol. 223, pp. 259-267.

Onda et al., "Cell Impedance Measurement by Laplace Transformation of Charge or Discharge Current-Voltage", Journal of the Electrochemical Society, 2006, vol. 153, No. 6, pp. A1012-A1018.

Schmidt et al., "Investigation of the Thermal Properties of a Li-ion Pouch-cell by Electrothermal Impedance Spectroscopy", Journal of Power Sources, 2011, vol. 196, pp. 8140-8146.

Wainwright "Method of Evaluating Relative Safety of Porous Electrode/Electrolyte Combinations to Spot Heating", Journal of Power Sources, 1995, vol. 54, pp. 192-197.

* cited by examiner

METHODS AND DEVICES FOR ELECTROCHEMICAL SYSTEM ANALYSIS

CONTRACTUAL ORIGIN

The United States Government has rights in this invention under Contract No. DE-AC36-08GO28308 between the United States Department of Energy and Alliance for Sustainable Energy, LLC, the Manager and Operator of the National Renewable Energy Laboratory.

BACKGROUND

Devices that consume electrical power are ubiquitous in today's society. Many of these devices rely on electrical power stored in batteries and other energy storage devices. Typically, for battery-powered devices, the batteries are charged when the device is not in use and are at least partially discharged as the device is used, thereby consuming the electrical power from the battery.

With the increasing importance of electronic devices, manufacturers are striving to make devices and batteries that run more efficiently (e.g., devices that consume less power and batteries that last longer on a single charge, generate less waste heat, etc.) and have a longer useful lifetime. In order to make more efficient batteries that have a longer lifetime, it can be important to understand various performance characteristics (e.g., heat generation, reliability, etc.) of components within a battery, such as the anode, the cathode, the electrolyte, or other components.

Calorimeters provide one way of measuring the heat energy created or consumed by a sample. Various types of calorimeters exist, such as adiabatic calorimeters, reaction calorimeters, bomb calorimeters, differential scanning calorimeters, and others. For instance, heat flux differential scanning calorimeters measure the temperature difference between a sample pan and a reference pan. Using calibration curves, the temperature difference between the sample and the reference pans allows for the heat flux to the sample under test to be calculated.

SUMMARY

In one aspect, the present disclosure describes a calorimeter device and methods of analyzing battery components. The calorimeter and/or analysis methods may be used to obtain more accurate measurement of heat generation by battery cells and other sample objects. Such improved results may enable cheaper battery production, longer-lasting batteries, and/or a better understanding of the safety and reliability of internal battery components.

In one example, a device includes a first thermo-electric gauge (TEG), and a first conductor thermally coupled to the first TEG, the first conductor comprising a surface and a first electrical connection. The device also includes a second conductor comprising a surface and a second electrical connection, wherein the surface of the second conductor is facing the surface of the first conductor, the surface of the first conductor and the surface of the second conductor forming a gap. The device additionally includes a second TEG thermally coupled to the second conductor, and an adjustment mechanism attached to the second TEG, operable to modify a size of the gap between the surface of the first conductor and the surface of the second conductor.

In another example, a method includes applying a plurality of electrical signals across an electrochemical system comprising a plurality of components, each of the plurality of electrical signals having a respective value of a characteristic, wherein the respective value of the characteristic of each of the plurality of oscillating electrical signals is associated with one or more respective components from the plurality of components. The method also includes determining, using a calorimeter, at least one rate at which heat is generated by the electrochemical system in response to the plurality of electrical signals, and determining, based on the at least one rate at which heat is generated in response to the plurality of electrical signals, at least one thermal characteristic of at least one component from the plurality of components.

The details of one or more examples are set forth in the accompanying drawings and the description below. Other features, objects, and advantages will be apparent from the description and drawings, and from the claims.

DETAILED DESCRIPTION

Figure 1:
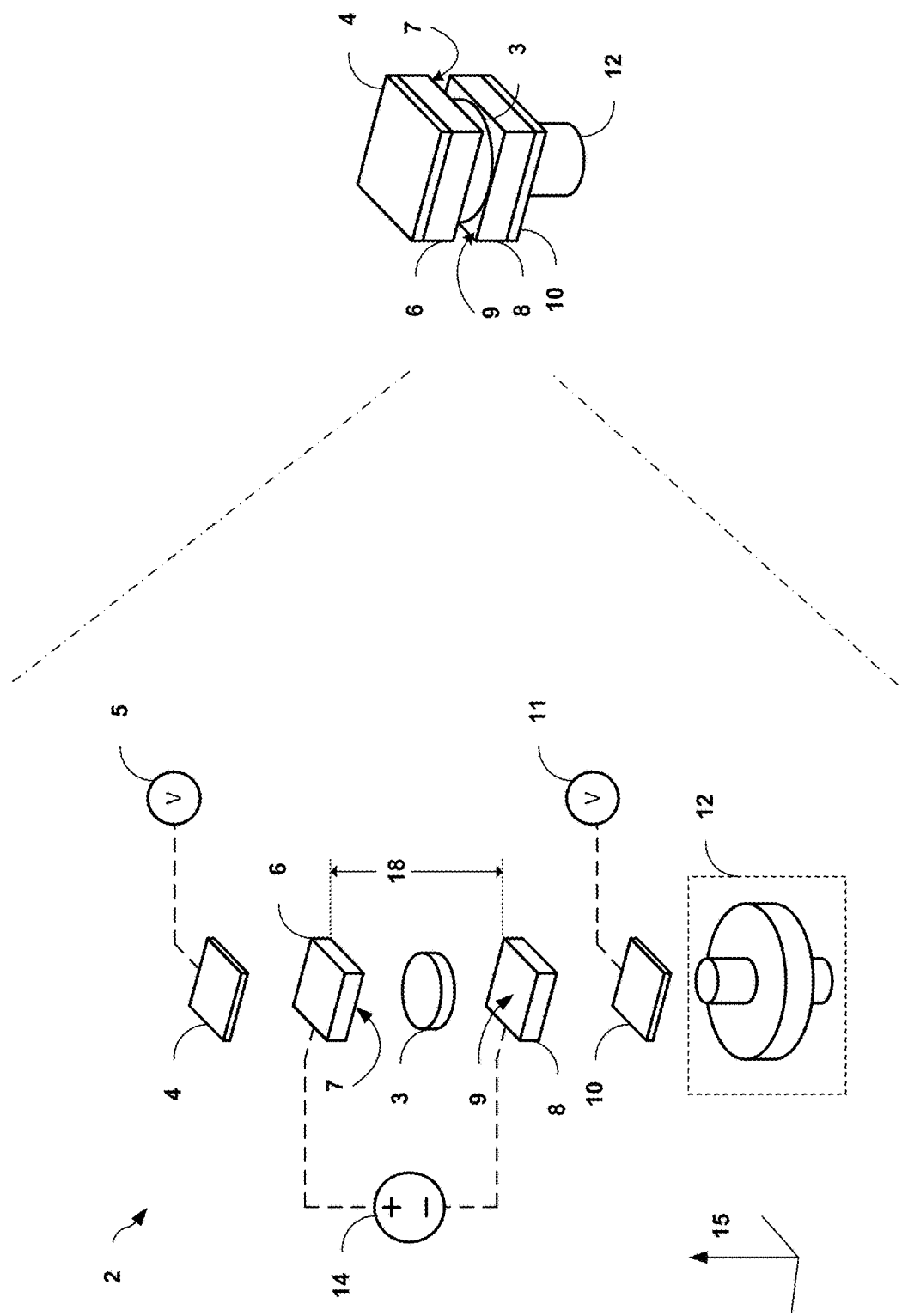
FIG. 1 is a diagram illustrating components of an example calorimeter assembly, in accordance with one or more aspects of the present disclosure.

In one aspect, the present disclosure describes a calorimeter designed to measure the heat energy of a substantially flat sample object such as a coin cell or button cell battery by holding the object between two thermal conductors such that heat energy from (or to) the object flows through the conductors and across two thermal electric gauges (TEGs) that measure heat flux. The calorimeter described herein includes an adjustment mechanism operable to increase and decrease the distance between the two conductors. The conductors, TEGs, and sample object may be enclosed in a chamber that is then placed in an isothermal bath, thereby further restricting thermal influence from outside the calorimeter.

The ability to modify the distance between the conductors using the adjustment mechanism may enable the calorimeter described herein to accommodate objects of different sizes while ensuring good contact between the surfaces of the object and the conductors. Improved thermal conductivity between a sample object and the measurement device may enable measurement of heat energy with improved accuracy and precision compared to related art devices. Additionally, the adjustment mechanism may enable additional uniformity in setup to improve measurement accuracy.

As another advantage, by directly measuring the heat energy flow on both sides of the object, the calorimeter described herein may provide particularized measurements that enable specialized analysis, such as determining how the two surfaces of the object heat differently. Such particularized measurements may enable the production of more efficient and/or cheaper devices. Furthermore, by placing the test chamber in an isothermal environment, the device described herein may provide accurate and precise measurements without using a secondary control chamber. That is, because the calorimeter described herein substantially reduces outside influence, comparison with a reference chamber may be unnecessary, thereby significantly reducing production cost of the device and improving accuracy, as using a single chamber reduces the amount of noise present in measurements. Due to its size and configuration, the calorimeter described herein may have a substantially lower response time and substantially lower noise level, enabling improved measurements of very small heat signals. For instance, the devices described herein may enable measurement of the heat generated by processes having a very small time constant.

In another aspect, the present disclosure describes methods for detailed analysis of components within an electrochemical system, such as a battery. In accordance with the techniques described herein, a series of electrical signals having different characteristics (e.g., frequencies, rates of change, durations, etc.) may be applied to the electrochemical system. The heat generated by the system in response to the signals may be measured using a calorimeter. The characteristics of the applied electrical signals may correlate to one or more specific components within the electrochemical system. Thus, by applying the signals, the methods of the present disclosure may enable detailed analysis of various components of the system by analyzing the heat generated in response to the signals.

The analysis techniques described herein may help battery manufacturers to determine which components in the battery produce the most heat. Furthermore, by repeatedly applying the series of electrical signals after successive power cycling of the system (e.g., charging and discharging of a battery), the techniques described herein may provide an indication of which components are likely to endure prolonged use of the battery, and which components are likely to fail. In some examples, the techniques of the present disclosure may be used in conjunction with the calorimeter described herein. In some examples, however, other calorimeters or devices may be used.

Figure 2:
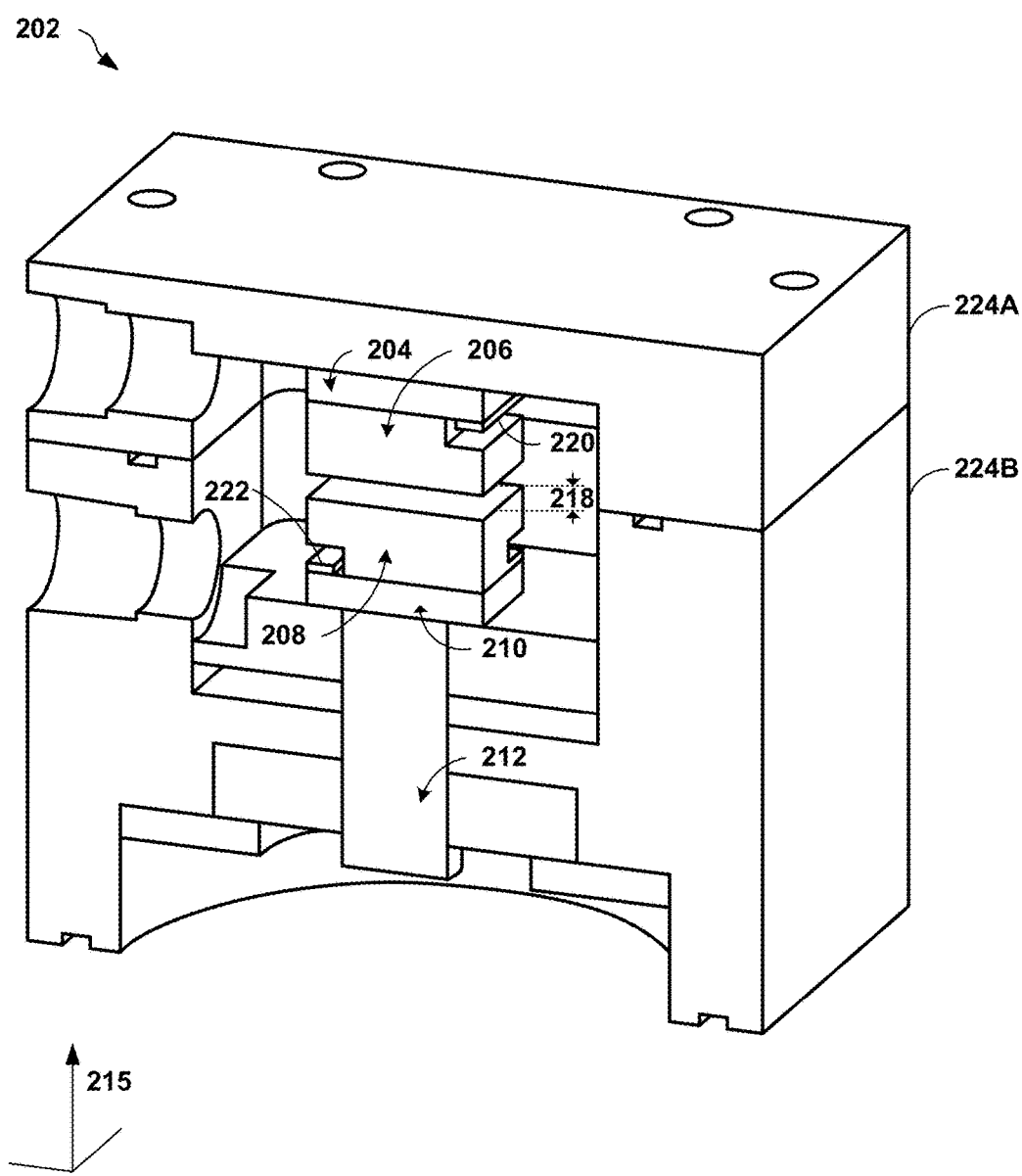
FIG. 2 is perspective diagram illustrating an example calorimeter assembly, in accordance with one or more aspects of the present disclosure.

FIG. 1 is a diagram illustrating components of example calorimeter assembly 2, in accordance with one or more aspects of the present disclosure. The left side of FIG. 1 illustrates an exploded view of the components of calorimeter assembly 2, while the right side of FIG. 1 illustrates the components together, as during operation, for instance. Calorimeter assembly 2 may be configured to apply one or more signals across an electrochemical system (e.g., coin cell battery 3) and measure the heat response of the system. FIG. 2 illustrates just one example calorimeter assembly. Other orientations, combinations, and/or components may be used in various examples.

In the example of FIG. 1, calorimeter assembly 2 includes a first TEG 4 and a second TEG 10. TEGs 4 and 10 may be sensors that measure thermal flux and output electrical signals indicating the thermal flux. That is, each TEG may measure the rate at which heat energy is transferred through the sensor and output an electrical signal proportional to the measured rate. As shown in the example of FIG. 1, TEGs 4 and 10 are connected to meters 5 and 11, respectively. Meters 5 and 11, as shown in the example of FIG. 1, are voltage meters, capable of measuring an electrical potential created by their respective TEGs. In some examples, meters 5 and 11 may be ammeters capable of measuring a current created by a connected TEG. For instance, TEGs 4 and 10 may be connected to a respective load (e.g., a resistor) and meters 5 and 11 may measure the current that flows through the load.

Calorimeter assembly 2, in the example of FIG. 1, also includes a first conductor 6 and a second conductor 8. Conductors 6 and 8 may be blocks of material that are thermally and electrically conductive. For instance, conductors 6 and 8 may be made of copper, silver, aluminum, and/or various other suitable material(s). Conductor 6 may be thermally coupled to TEG 4 and conductor 8 may be thermally coupled to TEG 10, such that heat energy may flow between each conductor and the respective TEG.

In the example of FIG. 1, conductor 6 includes surface 7 and conductor 8 includes surface 9. Surfaces 7 and 9 may be suitable for contact with respective surfaces of a sample object, such as coin cell battery 3. As shown in the example of FIG. 1, for instance, surface 7 of conductor 6 is facing negatively along axis 15 and surface 9 of conductor 8 is facing positively along axis 15. Surfaces 7 and 9 may form a gap 18. During operation of the calorimeter, battery 3 may be placed into gap 18 for analysis. In the example of FIG. 1, surfaces 7 and 9 are substantially flat and parallel to one another. In some examples, surfaces 7 and 9 may be skewed. In some examples, one or both of surfaces 7 and 9 may be curved, multi-planar, or otherwise not flat. In other words, one or both of surface 7 and surface 9 may be different in various examples.

Conductor 6 and conductor 8 may each include an electrical connection for receiving an electrical input signal. For instance, as shown in the example of FIG. 1, conductor 6 and conductor 8 may be connected to signal generator 14. During operation of the calorimeter as shown in the example of FIG. 1, signal generator 14 may be used to transmit an electrical input signal from one conductor to the other, across battery 3.

Calorimeter assembly 2, as shown in the example of FIG. 1, includes adjustment mechanism 12. Adjustment mechanism 12 may be attached to TEG 10 and may be operable to modify a size of gap 18 between surfaces 7 and 9. For instance, adjustment mechanism 12 may increase and decrease the size of gap 18 by moving conductor 8 and TEG 10 negatively and positively along axis 15. Adjustment mechanism 12 may be used to enlarge gap 18 when inserting a larger sample object for measurement. Adjustment mechanism 12 may be used to reduce gap 18 when inserting a smaller sample object for measurement and/or to ensure optimum surface contact area between surfaces 7 and 9 and the sample object. For instance, adjustment mechanism 12 may be a spring-loaded mechanism, a screw-type mechanism, or other adjustment mechanism.

In accordance with the techniques described herein, calorimeter assembly 2, as shown in the example of FIG. 1, may be used to analyze the heating of battery 3 in response to one or more applied input signals. Battery 3 may be placed in gap 18, and adjustment mechanism 12 may be used to move conductor 8 and TEG 10 positively along axis 15 to ensure that surfaces 7 and 9 are both in contact with surfaces of battery 3. Signal generator 14 may then be used to apply one or more signals across battery 3. Heat generated by battery 3 may be conducted through conductors 6 and 8 to TEGs 4 and 10. TEGs 4 and 10 may generate electrical signals indicating the heat flux, and meters 5 and 11 may measure the electrical signals, thereby indicating the amount of heat generated by battery 3.

A calorimeter configured as described herein may enable more accurate and precise measurements of how various sample objects heat up during use. Including a TEG on both sides of the sample object may enable more detailed analysis by providing information about how different surfaces of the sample object heat differently during operation and/or testing. Additionally, such a calorimeter may be cheaper and easier to produce. For instance, by ensuring optimum contact and conduction between the surfaces of the sample object and the TEGs, a calorimeter as described herein may ensure that the vast majority of heat energy flows through the TEGs and thus numerous TEGs may not be necessary. The calorimeter also achieves accurate and precise measurements without having a second, control chamber, thereby further increasing accuracy (e.g., by reducing noise) and reducing production cost. That is, by not including a second chamber, the device described herein may remove variability in measured quantities between the two chambers. In addition, such an improved calorimeter may enable detailed analysis methods as further described herein with respect to FIGS. 5-9.

FIG. 2 is a perspective diagram illustrating example calorimeter assembly 202, in accordance with one or more aspects of the present disclosure. In the example of FIG. 2, calorimeter assembly 202 has been sectioned into two portions. FIG. 2 shows only a first section of calorimeter assembly 202 in order to provide a view of interior components.

In the example of FIG. 2, calorimeter assembly 202 includes TEGs 204 and 210, conductors 206 and 208, and adjustment mechanism 212. Components 202, 204, 206, 208, 210, and 212 may be substantially similar to components 2, 4, 6, 8, 10 and 212, respectively, as described with respect to FIG. 1.

Conductors 206 and 208 may include respective surfaces forming gap 218. During operation of the calorimeter, a sample object may be placed into gap 218 for analysis. Conductor 206 and conductor 208 may also each include a respective electrical connection for receiving an electrical input signal. For instance, as shown in the example of FIG. 2, conductor 206 includes electrical connection 220 and conductor 208 includes electrical connection 222. During operation of the calorimeter, electrical connections 220 and 222 may be used to transmit an electrical input signal from one conductor to the other, across a sample object. Further details of one example conductor are described with respect to FIG. 4, below.

TEG 204, conductor 206, conductor 208, and TEG 210, in the example of FIG. 2, are located within a recessed cavity formed by housing 224A and 224B (collectively, "housing 224"). Housing 224A may be referred to as a body portion and housing 224B may be referred to as a lid portion. Together, housing 224 may form a substantially enclosed cavity that contains TEGs 204 and 210 and conductors 206 and 208. In some examples, housing 224 may have one or more apertures or openings, such as openings for maintaining connections (not shown) to electrical connectors 220 and 222 while housing 224 is closed. As another example, housing 224 may have openings for electrical connections to TEGs 204 and 210 or other components. Otherwise, housing 224 may serve as a physical barrier separating calorimeter assembly 202 from the exterior of housing 224. That is, the cavity formed by housing 224 may be substantially enclosed in that the cavity has only limited accessibility.

In accordance with the techniques described herein, calorimeter assembly 202 may be used to analyze various sample objects, such as a button cell battery or other electrochemical system. Prior to operation, a sample object, such as a button cell battery may be placed in gap 218. Housing 224A may be affixed to housing 224B, thereby substantially sealing TEGs 204 and 210, and conductors 206 and 208, within housing 224.

Adjustment mechanism 212 may be used to move conductor 208 and TEG 210 positively or negatively along axis 215 to ensure that the surface of conductor 206 and the surface of conductor 208 are both in contact with surfaces of the sample object. That is, adjustment mechanism 212 may be used to ensure optimum contact between the sample object and conductors 206 and 208. Housing 224 may be submerged in a containment unit (not shown). In some examples, the containment unit may be filled with liquid, such as water. The liquid in the containment unit may be brought to and maintained at a constant temperature throughout analysis of the sample object in order to reduce any outside thermal interference during measurement.

An input signal may be applied across the sample object, and the resulting heat response of the sample object may be indicated by TEGs 204 and 210. Based on one or more measured heat responses, various characteristics about components within the sample object may be determined. Such techniques are further described herein.

Figure 3A:
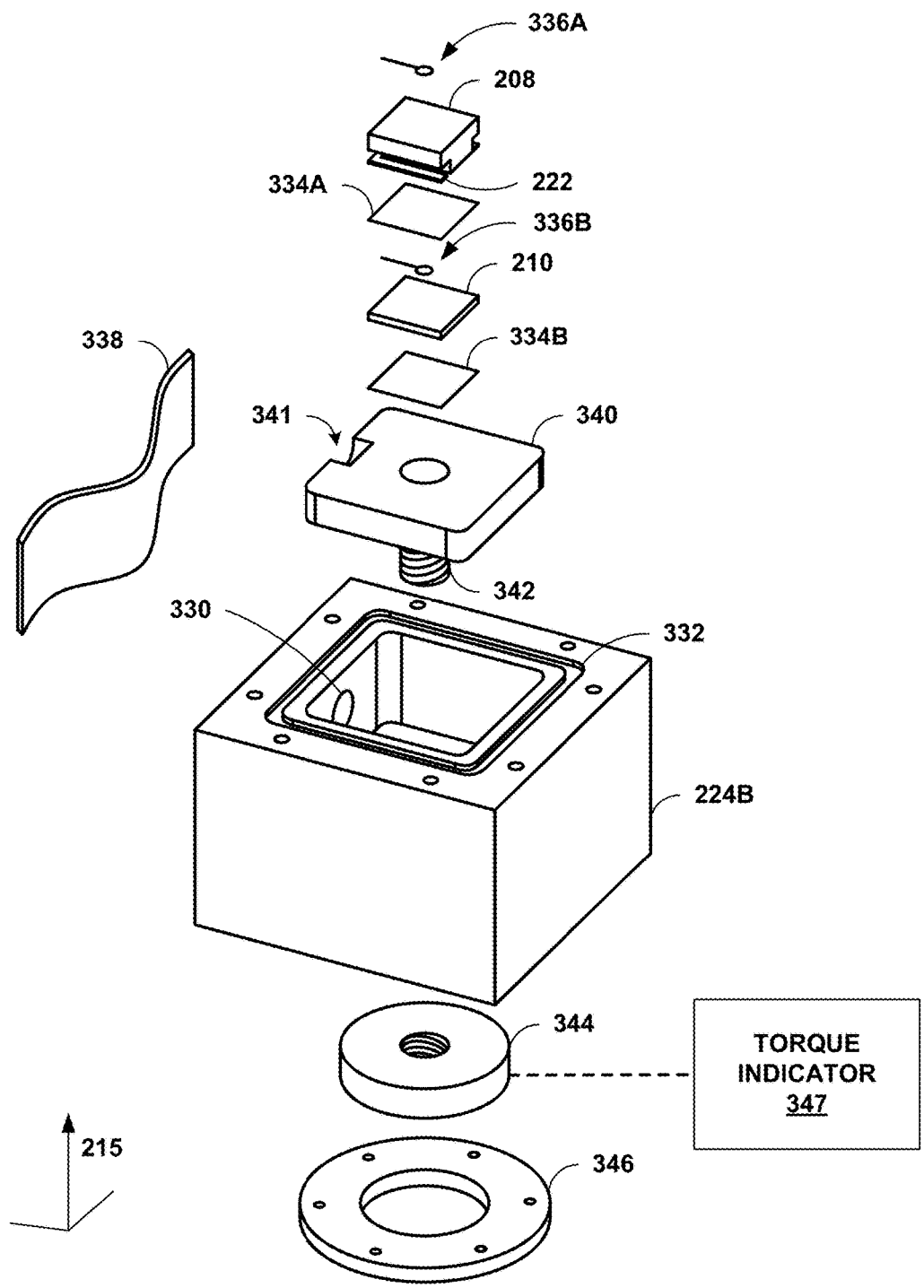
FIGS. 3A and 3B are exploded perspective diagrams illustrating further details of the example calorimeter assembly shown in FIG. 2.
Figure 3B:
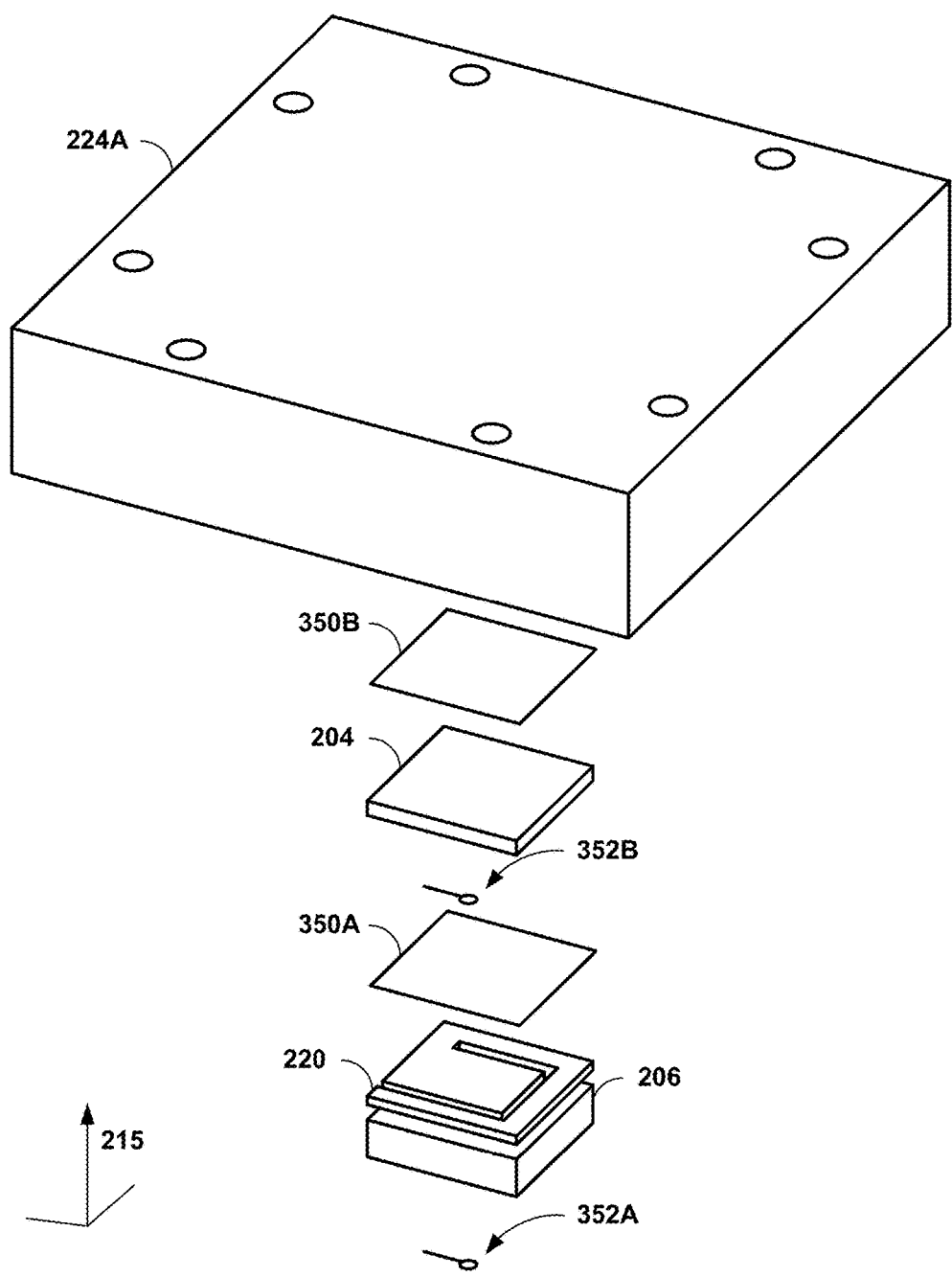

FIGS. 3A and 3B are exploded perspective diagrams illustrating further details of calorimeter assembly 202 described with respect to FIG. 2. In the example of FIG. 3A, calorimeter assembly 202 includes conductor 208, TEG 210, and housing 224B as described with respect to FIG. 2.

Housing 224B of calorimeter assembly 202, as shown in the example of FIG. 3A, includes aperture 330. Aperture 330 may provide access to the cavity formed by housing 224B during operation. For instance, Aperture 330 may be used as a conduit for connecting inputs to electrical connections 220 and 222, connecting outputs to TEGs 204 and 210, or other connections used during operation of calorimeter assembly 202. During operation, aperture 330 may be sealed, to ensure that the chamber formed by housing 224B and 224A, when attached, remains airtight. As one example, with all connections in place, aperture 330 may be filled with a sealant to fill in the remaining space.

As shown in the example of FIG. 3A, housing 224B also includes trough 332. Trough 332 may be a recess along the surface of housing 224B that attaches to housing 224A. In some examples, trough 332 may be filled with a sealant (not shown) in order to make the connection between housing 224A and housing 224B airtight. For instance, trough 332 may include a gasket made of rubber, silicone, or other suitable material. As additional examples, trough 332 may be filled with a sealant foam or liquid. As a result, the chamber formed when housing 224A is attached to housing 224B may be substantially airtight.

Calorimeter assembly 202, as shown in the example of FIG. 3A, also includes thermal interface material 334A, disposed between conductor 208 and TEG 210, and thermal interface material 334B, disposed between TEG 210 and heat plate 340. Thermal interface materials 334A and 334B (collectively "thermal interface materials 334") may be any substance or material usable to improve the thermal conductance between two components. In other words, thermal interface materials 334 may make it easier for heat energy to flow between the components. Thus, thermal interface materials 334 may improve the flow of heat energy from conductor 208, across TEG 210, and to heat plate 340.

Examples of thermal interface materials 334 may include thermal interface pads or tape made of silicone, acrylic, and/or any other suitable substance(s). In some such examples, thermal interface materials 334 may include adhesive on one or both sides of the pad or tape. As another example, thermal interface materials 334 may be a thermal paste, grease, or gel.

In some examples, thermal interface materials 334 may be substantially electrically insulating. That is, in some examples thermal interface materials 334 may not conduct electricity. By electrically insulating TEG 210 from conductor 208 and heat plate 340, thermal interface materials 334 may improve the accuracy of heat flux measurements obtained by TEG 210. Furthermore, electrically insulating conductor 208 from TEG 210 may help to ensure that any signal applied (e.g., via electrical connection 22) across a sample object does not take an alternate path, such as travelling through TEG 210 into heat plate 340 and/or housing 224B.

Conductor 208 and thermal interface materials 334 may ensure that the maximum amount of the thermal energy generated by a sample object is quickly transmitted to and detected by TEG 210. Compared to related art devices, this quick and efficient transfer of heat energy may enable calorimeter assembly 202 to detect thermal signals with very low time constants and/or very small magnitudes.

In the example of FIG. 3A, calorimeter assembly 202 includes voltage sensors 336A and 336B (collectively "voltage sensors 336"). Voltage sensor 336A may be attached to the surface of conductor 208 that will contact a sample object. Voltage sensor 336B may be disposed between conductor 208 and TEG 210. While shown in the example of FIG. 3A as being underneath thermal interface material 334A, voltage sensor 336B may, in various examples, be disposed above thermal interface material 334A, within thermal interface material 334A (e.g., when thermal interface material 334A is a thermal paste or grease), or otherwise disposed between conductor 208 and TEG 210.

Voltage sensors 336 may be configured to measure electrical potential, with 336A measuring the potential at the point of contact with the sample object and 336B measuring the potential at TEG 210. During operation of calorimeter assembly 202, electrical connection with voltage sensors 336 may be made through aperture 330 of housing 224B. Monitoring the voltage at the point of contact with the sample object may enable more accurate measurements of the exact signal being applied across the sample object. Furthermore, the difference in voltage between the point of contact with the sample object and the surface of TEG 210 can be used to determine the electrical resistance of conductor 208 and thus the heat generated by conductor 208. That is, voltage sensors 336 may be used to determine how much heat is generated by conductor 208, and this additional heat can be accounted for to achieve more accurate measurements of the heat being generated by the sample object.

Calorimeter assembly 202, as shown in the example of FIG. 3A, also includes insulation 338. During operation of calorimeter assembly 202, insulation 338 may be disposed in the cavity formed by housing 224, between the inner wall of housing 224 and one or more of components 208, 210, 334A, and 334B. Insulation 338 may be any material that reduces thermal conductivity. In some examples, insulation 338 may be a solid material, such as Asbestos or other insulating material. In some examples, insulation 338 may be a liquid or a gas, such as aerogel, closed cell foam, open cell foam, helium, nitrogen, or even air. Insulation 338 may reduce the transfer of heat energy from the components to the surrounding environment, thereby increasing the likelihood that the heat energy is conducted across TEG 210 and thus measured.

In the example of FIG. 3A, calorimeter assembly 202 also includes heat plate 340. Heat plate 340 may serve as a movable part of housing 224B. Heat plate 340 may move positively or negatively along axis 215 with operation of adjustment mechanism 212, thereby increasing or decreasing the size of the cavity formed by housing 224B. That is, any adjustments made to adjustment mechanism 212 may cause heat plate 340, along with TEG 210, thermal interface materials 334, and conductor 208, to move up or down. In this way, heat plate 340 may ensure that the cavity is as small as possible given the size of the sample object, thereby reducing potential error in measurements during use of calorimeter assembly 202.

Heat plate 340 may be made of any suitable, thermally conductive material, such as aluminum or copper. As heat energy propagates from conductor 208 and across TEG 210, the heat energy may be conducted into heat plate 340 (e.g., via thermal interface material 334B). The sides of heat plate 340 may be substantially in contact with the inner wall of housing 224B that forms the cavity in which heat plate 340 resides. For instance, the sides of heat plate 340 may be physically touching the inner wall of housing 224B, be within a few micrometers of the inner wall, or within a few millimeters. In some examples, while the sides of heat plate 340 are substantially in contact with the inner wall of housing 224B, thermal grease or other substance(s) may be disposed between the sides of heat plate 340 and the inner wall of housing 224B to improve the thermal conductivity between the two components.

In some examples, heat plate 340 may be notched to allow access to aperture 330 of housing 224B. For instance, heat plate 340 may include notch 341, as shown in the example of FIG. 3A. In some examples, heat plate 340 may not include any notches. In other examples, heat plate 340 may include more than one notch (e.g., notches on different sides of heat plate 340). In other words, heat plate 340 may, in some examples, be configured such that openings in housing 224B remain accessible from inside the cavity formed by housing 224B and heat plate 340 despite movement of the heat plate 340 via adjustment mechanism 212.

Calorimeter assembly 202, in the example of FIG. 3A, includes shaft 342, adjustment hub 344, and friction plate 346. Shaft 342, adjustment hub 344, and friction plate 346 may collectively represent one example of adjustment mechanism 212 as described with respect to FIG. 2. That is, shaft 342, adjustment hub 344, and friction plate 346 may collectively be operable to modify the size of gap 218 described with respect to FIG. 2.

Shaft 342 may be attached to heat plate 340 (e.g., thereby being attached to conductor 208 and TEG 210) and disposed at least partially within the cavity formed by housing 224B. Adjustment hub 344 may be disposed underneath housing 224B, outside the cavity. Adjustment hub 344 may be held in place under housing 224B by friction plate 346, attached to housing 224B. That is, during operation of calorimeter assembly 202, adjustment hub 344 may be essentially stuck between friction plate 346 and housing 224B. For instance, friction plate 346 may ensure that adjustment hub 344 does not rotate around axis 215 of its own accord. Furthermore, friction plate 346 may ensure that adjustment hub 344 is unable to move any substantial amount along axis 215 or transverse to axis 215.

In the example of FIG. 3A, the outer wall of shaft 342 and the inner wall of adjustment hub 344 may be oppositely threaded such that shaft 342 may act as a nut and adjustment hub 344 may at as a bolt. That is, when shaft 342 is properly placed in adjustment hub 344, any angular force around axis 215 that turns adjustment hub 344 may be translated into vertical force that moves shaft 342 positively or negatively along axis 215. Consequently, in the example of FIG. 3A, adjustment mechanism 212 may be used through rotation of adjustment hub 344.

Turning to FIG. 3B, calorimeter assembly 202 also includes TEG 204, conductor 206, and housing 224A as described with respect to FIG. 2. Calorimeter assembly 202, as shown in the example of FIG. 3B, also includes thermal interface material 350A, disposed between conductor 206 and TEG 204, and thermal interface material 350B, disposed between TEG 204 and housing 224A. Thermal interface materials 350A and 350B (collectively "thermal interface materials 350") may be any substance or material usable to improve the thermal conductance between two components. In other words, thermal interface materials 350 may make it easier for heat energy to flow between the components. Thus, thermal interface materials 350 may improve the flow of heat energy from conductor 206, across TEG 204, and to heat plate housing 224A.

Examples of thermal interface materials 350 may include thermal interface pads or tape made of silicone, acrylic, and/or any other suitable substance(s). In some such examples, thermal interface materials 350 may include adhesive on one or both sides of the pad or tape. As another example, thermal interface materials 350 may be a thermal paste, grease, or gel.

In some examples, thermal interface materials 350 may be substantially electrically insulating. That is, in some examples thermal interface materials 350 may not conduct electricity. By electrically insulating TEG 204 from conductor 206 and housing 224A, thermal interface materials 350 may improve the accuracy of heat flux measurements obtained by TEG 204. Furthermore, electrically insulating conductor 206 from TEG 204 may help to ensure that any signal applied (e.g., via electrical connection 20) across a sample object does not take an alternate path, such as travelling through TEG 204 into housing 224A.

Calorimeter assembly 202, in the example of FIG. 3B, includes voltage sensors 352A and 352B (collectively "voltage sensors 352"). Voltage sensor 352A may be attached to the surface of conductor 206 that will contact a sample object. Voltage sensor 352B may be disposed between conductor 206 and TEG 204. While shown in the example of FIG. 3B as being above thermal interface material 350A, voltage sensor 352B may, in various examples, be disposed below thermal interface material 350A, within thermal interface material 350A (e.g., when thermal interface material 350A is a thermal paste or grease), or otherwise disposed between conductor 206 and TEG 204.

Voltage sensors 352 may be configured to measure electrical potential, with 352A measuring the potential at the point of contact with the sample object and 352B measuring the potential at TEG 204. During operation of calorimeter assembly 202, electrical connection with voltage sensors 352 may be made through aperture 330 of housing 224B as described with respect to FIG. 3A. Monitoring the voltage at the point of contact with the sample object may enable more accurate measurements of the exact signal being applied across the sample object. Furthermore, the difference in voltage between the point of contact with the sample object and the surface of TEG 204 can be used to determine the electrical resistance of conductor 206 and thus the heat generated by conductor 206. That is, voltage sensors 352 may be used to determine how much heat is generated by conductor 206, and this additional heat can be accounted for to achieve more accurate measurements of the heat being generated by the sample object.

In the example of FIGS. 3A and 3B, calorimeter assembly 202 may be operated by placing a sample object (e.g., a coin cell battery) on top of conductor 208 and attaching housing 224A to housing 224B, thereby creating a substantially airtight chamber. Thereafter, adjustment hub 344 may be rotated to ensure that the surfaces of the coin cell battery have good contact with the surfaces of conductors 206 and 208. For instance, prior to sealing of housing 224, adjustment hub 344 may be turned such that heat plate 340, TEG 210, and conductor 208 are maximally adjusted negatively along axis 215. Then, after sealing of housing 224, adjustment hub 344 may be used to move heat plate 340, TEG 210, and conductor 208 positively along axis 215 until sufficient contact between the sample object and conductors 206 and 208 is obtained.

One example method for determining adequate contact is by measuring the amount of torque necessary to turn adjustment hub 340. For instance, torque indicator 347 may be used to measure the angular force necessary to further turn adjustment hub 340 (thereby raising heat plate 340). As one example, torque indicator 347 may represent a torque wrench usable to turn adjustment hub 340. In other examples, torque indicator 347 may be any mechanism capable of determining the torque applied to adjustment hub 340.

Using torque indicator 347, sufficient contact may be established when a pre-defined level of torque becomes necessary to further turn adjustment hub 340. Other example methods for determining adequate contact may utilize resistance between the conductors and the sample object, surface area measurements, or other objective quantities. Relying on such objective measurements to determine contact may yield improved results, as such values may be re-applied in various experiments, regardless of sample object size.

Once calorimeter assembly 202 is properly set up with the sample object inside, voltage and heat measurements may be made using signals received from voltage sensors 336 and 352, and TEGs 204 and 210. Additionally, input signals can be applied to the sample object through electrical connections 220 and 222. Additional details and example methods of operation are described with respect to FIGS. 5-9, below.

Figure 4:
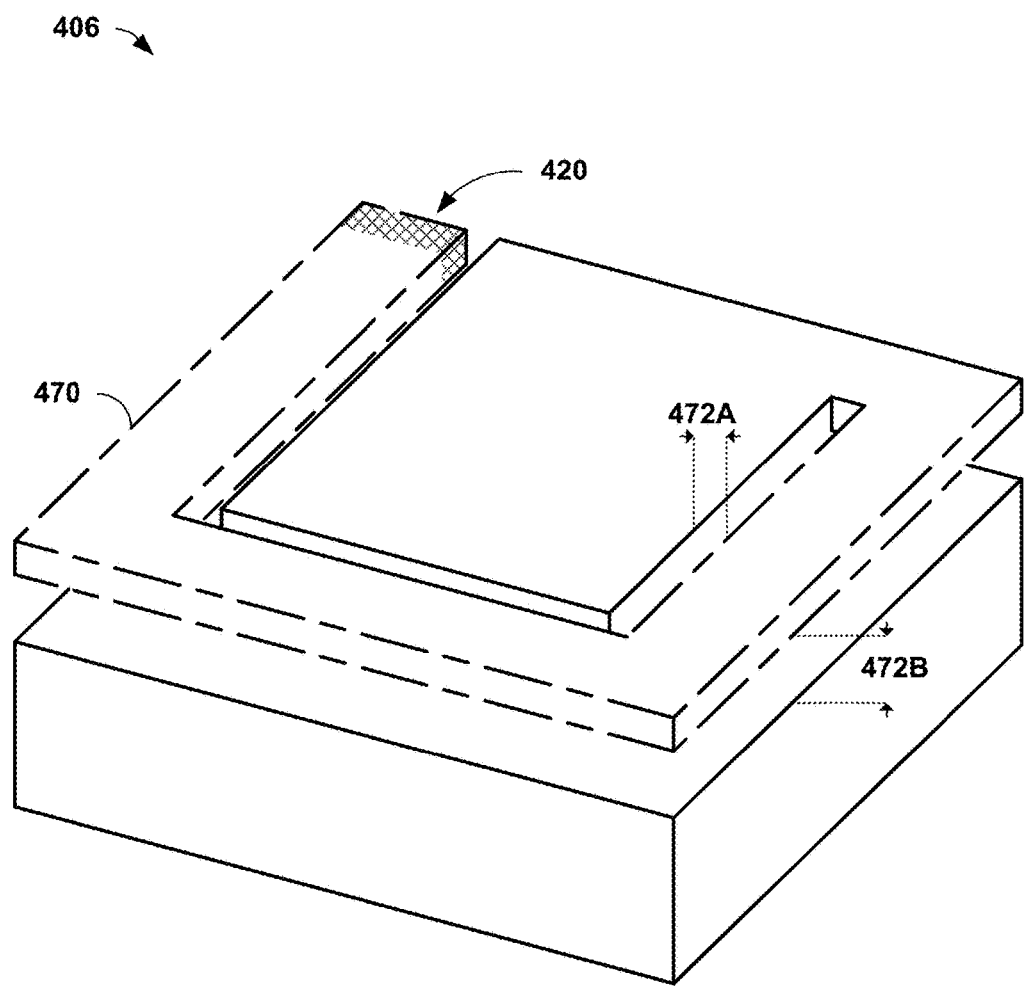
FIG. 4 is a perspective diagram illustrating one example of a thermoelectric conductor, in accordance with one or more aspects of the present disclosure.

FIG. 4 is a perspective diagram illustrating example conductor 406, in accordance with one or more aspects of the present disclosure. Conductor 406 may represent one example of conductors 206 and 208, as described with respect to FIGS. 1-3. However, various other shapes and configurations of conductors may be used in accordance with the present disclosure. In the example of FIG. 4, conductor 406 includes electrical connection 420 and busbar 470. Conductor 406 also includes recesses 472A and 472B (collectively "recesses 472").

Electrical connection 420, in the example of FIG. 4, is shown as the crosshatched portion of busbar 470. Electrical connection 420 may have functionality similar to that described with respect to electrical connections 220 and 222 of FIGS. 2 and 3. That is, electrical connection 420 may be one point of contact for applying an input signal across a sample object. In some examples, electrical connection 420 may be a point at which wire (not shown) can be electrically connected (e.g., using solder, via an alligator clip, or other means) to conductor 406. In some examples, electrical connection may be a plug or jack into which an input may be inserted. In any case, electrical connection 420 may be at an end of busbar 470.

In the example of FIG. 4, busbar 470 is shown using dotted lines to differentiate busbar 470 from the rest of conductor 406. That is, busbar 470 may be an arm extending from a main portion of conductor 406. One end of busbar 470 may be attached to the main portion of conductor 406 and the other end of busbar 470 (e.g., electrical connection 420) may not be connected to the main portion of conductor 406. In some examples, conductor 406 and busbar 470 may be fashioned from a single piece of material. In other examples, busbar 470 may be created separately and attached to conductor 406 in some fashion (e.g., welding, soldering, etc.). In some examples, busbar 470 may be made of the same material as the rest of conductor 406 while in other examples, busbar 470 may be made of different materials. The configuration of busbar 470 with respect to the rest of conductor 406 may allow electricity to flow relatively freely between electrical connection 420 and the surface of conductor 406 that is in contact with a sample object. However, busbar 470 may restrict the flow of thermal energy along the same path. In this way, busbar 470 may improve measurements by ensuring that minimal heat energy is lost to any wires or other attachments made at electrical connection 420 while still allowing for the application of an electrical signal.

As one way of reducing the transfer of thermal energy, busbar 470, as shown in the example of FIG. 4, is separated from the main portion of conductor 406 by recesses 472. By reducing the contact area between busbar 470 and the rest of conductor 406, recesses 472 may restrict any heat energy that would be conducted through busbar 470 to a smaller cross-section. In other words, recesses 472 ensure that heat has a smaller opening and must travel further (e.g., through the entirety of busbar 470) to reach electrical connection 420.

As another way of reducing the transfer of thermal energy, busbar 470, in some examples, may have a surface that is substantially flush with the surface of conductor 406 that will be in contact with a TEG. In this way, busbar 470 may also be in contact with the TEG, and any heat energy that does leak into busbar 470 may be conducted from that surface to the TEG (and thus be measured), instead of travelling down busbar 470 to electrical connection 420.

In the example of FIG. 4, busbar 470 is shown circumscribing almost three of the four sides of conductor 406. In some examples, busbar 470 circumscribes at least a portion of a perimeter of the surface of conductor 406 that is to be in contact with a TEG. In some examples, busbar 470 may be differently configured. For instance, busbar 470 may be a straight beam leading away from conductor 406, or may form a small spiral, traversing at least some sides of conductor 406 more than once. Regardless, recesses 472 may provide an air gap that restricts thermal energy being transferred to busbar 470, and busbar 470 may, in turn, reduce or eliminate thermal leakage through electrical connection 420.

Figure 5:
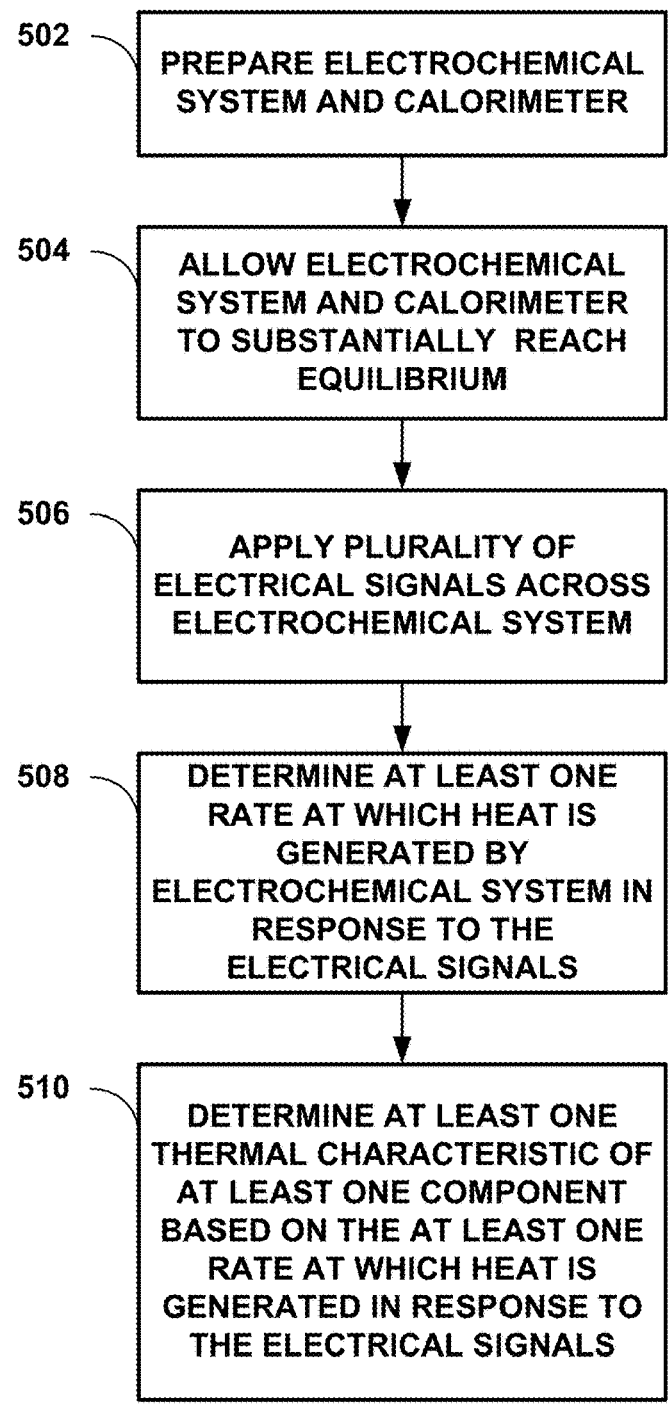
FIG. 5 is a flowchart illustrating example operations for analyzing components of an electrochemical system, in accordance with one or more aspects of the present disclosure.

FIG. 5 is a flowchart illustrating example operations for analyzing components of an electrochemical system, in accordance with one or more aspects of the present disclosure. For purposes of illustration only, the example operations of FIG. 5 are described below within the context of FIGS. 2 and 3. In other examples, however, the example operations of FIG. 5 may be performed using other calorimeters or other suitable devices.

In the example of FIG. 5, the electrochemical system and calorimeter assembly is prepared (502). For example, the electrochemical system may be a sample object, such as a coin cell or button cell battery. The cell may be placed into gap 218 of calorimeter assembly 202. Housing 224A and 224B (i.e., the top and bottom lids, respectively) may be put together and attached (e.g., via screws, fasteners, etc.). In some examples, a gasket may be disposed between housing 224A and 224B (e.g., in trough 332) to ensure a proper seal. A voltage of the electrochemical system may be monitored to ensure that there are no short-circuits and that the contacts between the electrochemical system and voltage sensors 336A and 352A are adequate.

Calorimeter assembly 202 may then be placed into an electrically insulated pouch and placed in an isothermal bath set to a target temperature. Generally, the bath may be a liquid bath, such as a water bath, a salt bath, a mineral oil bath, a hydrocarbon-based bath, or others. However, gaseous baths (e.g., air, nitrogen, etc.) or other baths may also be used. The bath may be maintained at a substantially constant temperature (e.g., within 0.001° C.). For example, the bath may be maintained using one or more temperature sensors with a feedback loop to heating coils positioned within the bath. In some examples, such as when a liquid bath is used, the bath is sized so that the liquid level in the bath is at least an inch above the topmost surface of the calorimeter assembly within the pouch.

The electrochemical system and calorimeter, in the example of FIG. 5, is allowed to substantially reach equilibrium (504). That is, calorimeter assembly 202 may be allowed to equilibrate in the bath. During this time, the voltage and heat output from the electrochemical system may be measured. Calorimeter assembly 202 may be considered to have reached equilibrium when the baseline heat flux, as measured by TEGs 204 and 210, does not oscillate more than a specified amount in a specified duration (e.g. 0.5 mW over one hour). The open circuit voltage (OCV) of the electrochemical system may be monitored during this duration.

In the example of FIG. 5, a plurality of electrical signals is applied across the electrochemical system (506). That is, the system may be electrically excited by imposing a voltage signal versus the OCV of the system. In some examples, each of the plurality of electrical signals may have a respective value of a characteristic, such as a frequency. In other words, the electrical signals may, in some examples, be periodic. In some examples, the signals may not be periodic. One example method for determining the respective signals for use in excitation of the electrochemical system is described with respect to FIG. 6, below.

In some examples, applying a voltage signal having a regular periodic form (e.g., a periodic pulse, a triangular wave, a sinusoidal wave, etc.) may yield more useful results because the electrical response of a battery cell under such controlled tests is predictable. For instance, a voltage pulse may be applied that lowers the cell voltage by 5 mV versus the OCV for a short duration (e.g., 0.5 seconds, 2 seconds, 5 seconds, or other duration). In response, the magnitude of the cell current may increase in proportion to its internal resistance over a duration that corresponds to the electrical time constants for the processes taking place within the battery. After this duration, the cell current may gradually reduce back to zero when the voltage equilibrium in the cell is restored. As another example, a sinusoidal perturbation of the voltage input may cause a response in which the current oscillates in a similar manner, but with a periodic lead or lag with respect to the frequency of the input signal.

When an electrochemical system is electrically excited, there may be several processes that take place simultaneously within the system. Each of these processes may have a different time constant for its response. For instance, the electronic flow across the highly conductive layers of a battery cell may have a time constant that is much smaller than that for the slow movement of the ions across the electrolyte of the battery cell. By varying certain characteristics (e.g., frequency, duration, amplitude, rate of change, etc.) of the input voltage signal and calculating the corresponding impedance of the battery cell, the electrical performance of the cell corresponding to the respective time constants of the different processes taking place within the cell may be interpreted. In other words, the respective characteristics of each of the plurality of electrical signals may be associated with one or more respective components or processes inside the electrochemical system.

In the example of FIG. 5, a calorimeter (e.g., calorimeter assembly 202) is used to determine at least one rate at which heat is generated by the electrochemical system in response to the plurality of electrical signals (508). For instance, TEGs 204 and 210 may measure the heat flux as each of the plurality of electrical signals is applied to the electrochemical system.

Due to the different response times of the processes in the electrochemical system, the various efficiencies of these processes, and the energetics accompanying each reaction, the corresponding heat generation rate and/or heat transfer across the different components for each of these processes may also be different. Thus, it may be possible to differentiate the heat generated from, for example, poor electronic conductivity across the electrode layers of a battery cell from the heat generated due to slow movement of ions within the electrolyte of the battery cell by measuring the heat signals from the cell when it is excited electrically by different signals.

In the example of FIG. 5, each of the plurality of electrical signals may be applied in succession and a respective rate at which heat is generated may be determined for each applied signal. As each electrical signal is applied, the heat flux may continue to increase while the rate of heat generation is larger than the rate of heat transfer away from the cell. That is, as the electrochemical system continues to emit increasing heat energy, TEGs 204 and 210 may indicate an increase in the rate at which heat energy flows across them. However, once the heat being transferred away from the cell substantially equals the heat being generated by the cell, the system will reach a new equilibrium and the heat flux may be considered "saturated" at the new level. In some examples, measuring the rate at which heat is generated may include determining the rate of heat dissipation during saturation.

In some examples, equilibrium while a signal is applied may be defined by the same criteria used to determine the initial equilibrium. That is, the system may be considered to be in equilibrium when the heat flux does not oscillate more than a specified amount in a specified duration (e.g. 0.5 mW over one hour). Once the heat flux achieves substantial equilibrium, the applied electrical signal may be turned off and the electrochemical system may be allowed to return to the baseline heat flux, where the system should remain stable.

Once the measurement of heat flux in response to the first signal is complete, the process may be repeated for the other signals, in sequence, as outlined above. Measurement of heat flux for each signal thus includes three stages: an initial equilibration stage, an excitation stage and a return to baseline stage. At each stage the heat signals may be measured until a substantially stable heat-signal (e.g., with oscillations less than or equal to 0.5 mW) is obtained.

At least one thermal characteristic of at least one component from the plurality of components is determined, in the example of FIG. 5, based on the respective rates at which heat is generated in response to the plurality of electrical signals (510). For instance, the dataset of experimentally obtained heat generation rates, whether obtained in the time domain as described with respect to the example of FIG. 5 or in the frequency domain as described below with respect to the example of FIG. 9, may be further utilized in conjunction with one or more electrochemical models of the electrochemical system to obtain physically meaningful parameters of the system, such as the activation energies and frequency factors for ion insertion as a function of state-of-charge, thermal diffusivities, or other parameters.

The physical parameters that characterize the performance of the electrochemical system may be obtained by regression of experimentally measured voltage- and/or temperature-versus-time data against a framework of model equations. The model equations may be, for example, the Navier-Stokes equations, modified to account for charge transport, in addition to species and energy transport. The regression technique may be a non-linear, least-squares fit, for example, based on the Nelder-Meade algorithm. The obtained physical parameters may be used to predict the performance of the cell under a different operating scenario such as a different ambient temperature or a different load condition.

While the electrochemical-thermal models in the frequency domain serve as a distinguishing factor in obtaining such useful characteristics, it is the availability of quality test data in conjunction with the theoretical tools that may maximize the battery design impact of the calorimeter assemblies and analysis methods described herein.

As one specific example, a fully charged lithium ion cell with a graphite-based anode and a transition metal oxide (e.g., $LiCoO_2$) cathode is saturated with lithium content on the anode compartment and has lower lithium stoichiometries in the cathode compartment. For such a device, the electrical conductivity at the anode is high and the cathode active material behaves like an insulator in the fully charged state. The calorimetric measurements from the heat-flux gauges on the anode-side versus those from the cathode side provides additional information on the heat fluxes associated with moving lithium ions in and out of the host-sites on either compartment and a measure of how well the entropic heats are matched. For instance, from low-frequency excitations (~0.5 mHz), it can be determined if there is excessive heat build-up on one of the electrode compartments, which will result in a drop in the thermal efficiency of the cell. At the medium frequencies (~10-~50 mHz) similar measurement of heat generation rates provides information on thermal losses during ionic conductivity in the electrolyte within each cell component. In such case, any heat buildup in one compartment versus another may provide insights on thermal inefficiencies due to mismatch in the porosity or thickness among the different cell components.

In some examples, obtaining a distinct thermal response from the applied signals may be contingent upon a number of test parameters, such as one or more characteristics (e.g., frequency, etc.) of the excitation signal, the OCV of the electrochemical system, the amplitude of the excitation signal (e.g., how far from the OCV the electrical signal for the excitation frequency deviates), the duration across which the measurement for a given signal is made, and others. The methods described herein may provide more accurate and precise results by ensuring that such parameters are tuned to produce the best results. For instance, the duration of measurement for each applied signal is calculated to compensate for the lag in the thermal response of the corresponding physical process or processes. As another example, the amplitude for the excitation signal may be varied with a signal frequency and/or the time-constant of the physical process in order to maintain meaningful heat generation rates across all time periods of interest. Furthermore, unlike electrical/electrochemical impedance techniques, in which the measurement conditions (e.g., the operating voltage) are solely determined based on the electrical properties of the individual components, in the techniques described herein, the operating parameters may also serve as an indication of the entropic heats associated with insertion/de-insertion of the ions at the corresponding voltage, and are thus determined based on the thermal properties of the components as well as the electrical properties.

Similar information and results cannot be attained from related art methods (e.g., Electrochemical Impedance Spectroscopy (EIS) or other electrical-only measurements) without the insertion of a third reference electrode within the cell. This is because the electrical characteristics of the individual components of an electrochemical system may not be sufficiently distinct from one another to allow separate identification. Installation of such a reference electrode can be an intrusive process that interferes with the performance of the original system and increases production cost and/or analysis cost.

The analysis methods described herein may be particularly useful for analyzing smaller electrochemical systems, as larger format cells (e.g., cells of capacity ranging from several hundred milliampere-hours to several ampere-hours) can generate a significant amount of ohmic heat due to the magnitude of the currents required to excite these cells. This effect may dominate or drown out the heat generation from other sources within the system, and result in less accurate measurements. Furthermore, performing such analysis using very low currents (micro-amps to milliamps) on a larger format cell or in a larger test set-up may necessitate very large time constants for measurement, during which time the heat signal generated by the cell may dissipate into the surroundings.

Using both the methods and the micro-calorimeter described in the present disclosure may improve the accuracy of the results, as performing such analysis methods on a coin cell (or cells of equivalent cell-capacity) using larger-format calorimeters may introduce interference in heat signals from the environment, say, due to oscillations in the baseline heat flux or due to lack of fidelity in measurement of the weak heat signals generated by the small format cells. That is, the calorimeter described herein may provide improved accuracy in conjunction with the described methods.

By allowing the heat flux to equilibrate and measuring the saturation heat flux, the techniques described herein may enable the capture of heat measurements that more accurately reflect the individual processes reacting to an applied voltage signal. That is, simply sweeping through signals having different characteristics (e.g., frequencies) may not provide adequate time to capture accurate heat signal information, as the heat generation corresponding to different electrical excitations may have a slower response time compared to the corresponding electrical response for the same excitation. Thus, using such a signal sweep may not allow for sufficient heat generation from all the processes of interest within the duration of electrical excitation. As a result, a deconvolution procedure that utilizes such data to resolve the combined heat flux from the cell into the heat flux from the individual frequencies may not fully capture the thermal efficacy of the specific process or processes that are excited by a signal of interest.

Figure 6:
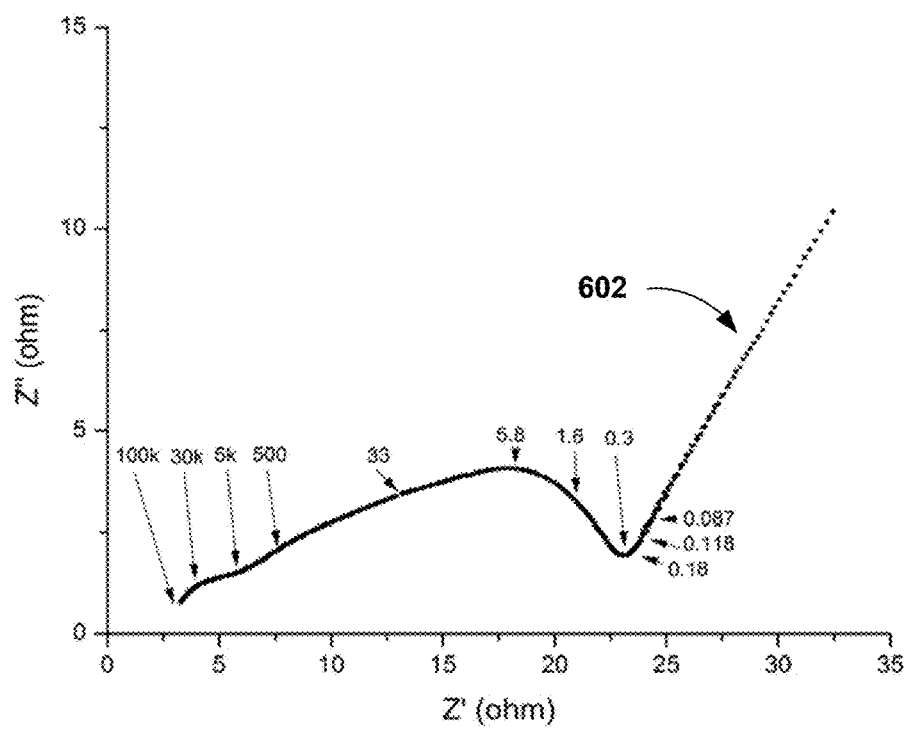
FIG. 6 is a graphical plot illustrating an example electrical response of an electrochemical system, in accordance with one or more aspects of the present disclosure.

FIG. 6 is a graphical plot illustrating example electrical response 602 of an electrochemical system, in accordance with one or more aspects of the present disclosure. Electrical response 602 may be obtained experimentally by applying various frequencies to an electrochemical system (e.g., using the calorimeter assembly described herein) and measuring the corresponding resistance of the system (e.g., using EIS). In the example of FIG. 6, the resistance at each frequency is plotted based on the real portion of the resulting impedance and the non-real portion of the resulting impedance.

Electrical response 602 may be used to determine a set of excitation frequencies for an electrochemical system (e.g., the same system used to obtain electrical response 602, another electrochemical system having similar chemistries, or other system). The excitation frequencies for the electrical input may be characteristic of the physical processes that take place within the cell. For example, the imaginary component of the impedance response, as shown in the example of FIG. 6, may be minimized in order to obtain heat signals from instantaneous ohmic heating of the cell. In other words, a frequency at which the electrical impedance intersects the abscissa may be preferable. As another example, to obtain the thermal response from diffusion, the range of excitation frequencies may be chosen such that the resulting electrical response shown in the example of FIG. 6 has a linear, positive slope. The determined excitation frequencies may then be used to apply signals as described with respect to the example of FIG. 5.

In some examples, determining the signals to apply across the electrochemical system may include determining, for each of the signals, a respective amplitude for causing optimum heat generation. The amplitudes may, in some examples, be determined based on a thermal mass of the electrochemical system components that are excited by the respective frequency. For instance, the amplitude may be chosen to ensure that the calorimeter will be able to measure the resulting heat flux (e.g., differentiate the heat flux from noise). For instance, under ideal ohmic conditions, if the amplitude used to measure the heat generated at 100 kHz is reduced by 50%, the corresponding heat flux will be reduced by 75%. However, such a reduction in amplitude may, in some examples, result in heat signals that are not sufficiently distinguishable from the baseline. Similarly, for a cell with identical performance but twice the mass, the heat dissipation rate may be twice as much under ideal conditions. Thus, amplitudes that are twice as large may be selected to ensure sufficient responses.

Figure 7:
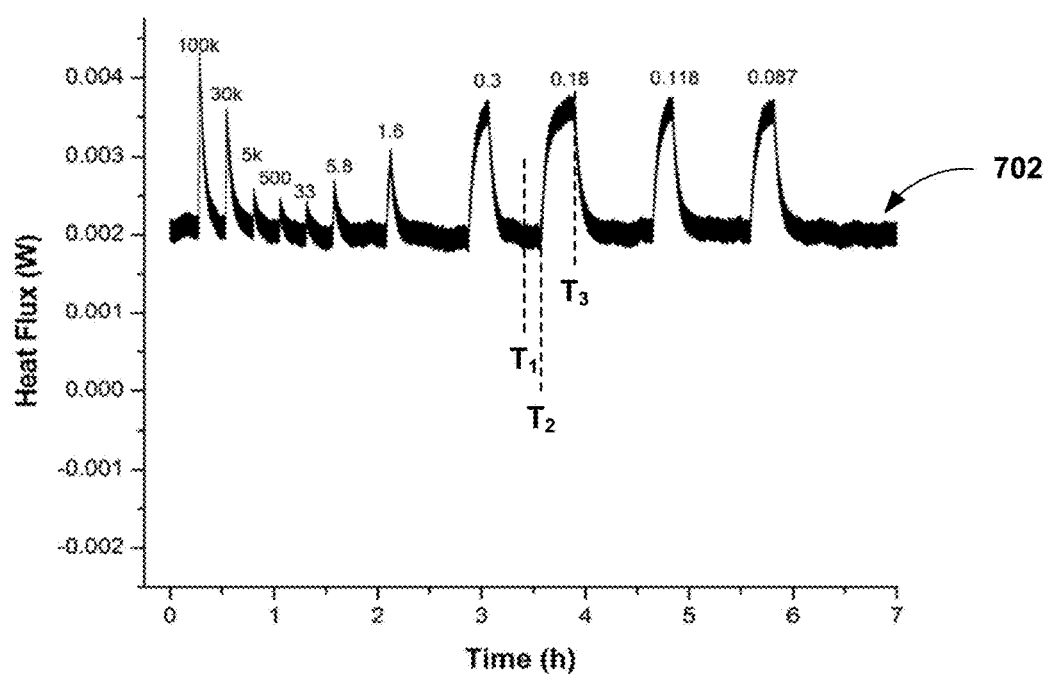
FIG. 7 is a graphical plot illustrating example heat flux measurements, in accordance with one or more aspects of the present disclosure.

FIG. 7 is a graphical plot illustrating example heat flux measurements 702, in accordance with one or more aspects of the present disclosure. Heat flux measurements 702 may, for example, be the result of performing the example method described with respect to FIG. 5 on a coin cell battery.

As shown in the example of FIG. 7, an equilibrium (or substantial equilibrium) may be initially established for the electrochemical system. Thereafter, a signal having a particular frequency may be applied across the electrochemical system. The heat flux may be measured until the flux substantially reaches a new equilibrium and then the signal may be removed. The system may be allowed to return to the baseline equilibrium, and the process may be repeated for additional frequencies. As one example, no signal may be applied at time $T_1$, and the heat flux may be allowed to return to baseline equilibrium. After reaching equilibrium, a signal with frequency 0.18 Hz may be applied to the system starting at $T_2$. The signal may be continuously applied until $T_3$, when the measured heat flux has saturated to a new equilibrium. Thereafter, the signal may be removed, and the heat flux may be allowed to return to baseline.

Figure 8:
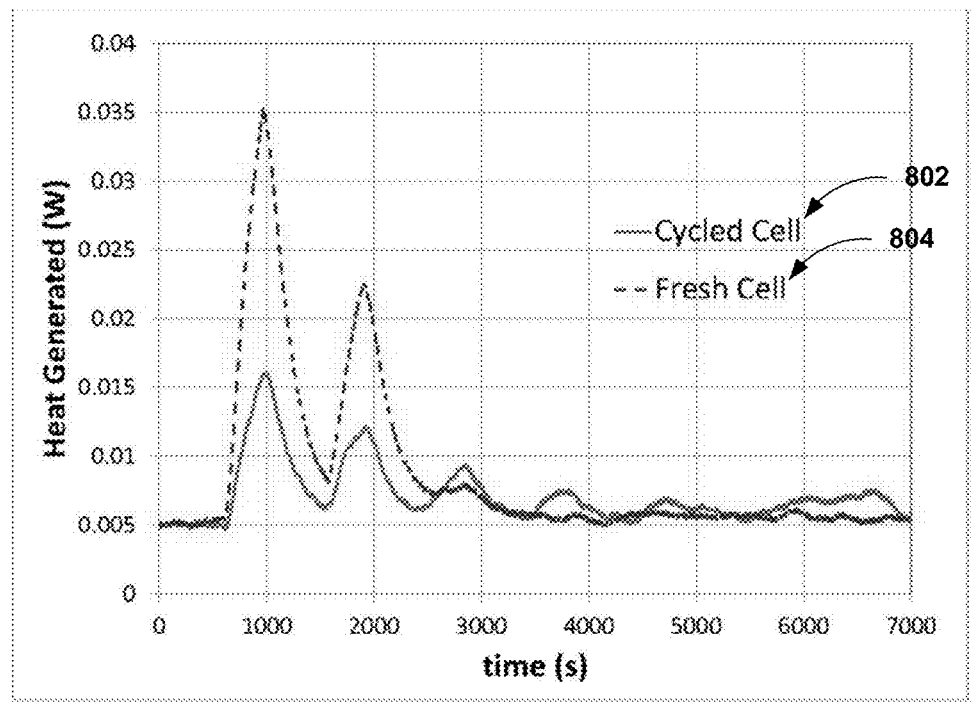
FIG. 8 is a graphical plot illustrating example heat flux measurements, in accordance with one or more aspects of the present disclosure.

FIG. 8 is a graphical plot illustrating example heat flux measurements 802 and 804, in accordance with one or more aspects of the present disclosure. Each of heat flux measurements 802 and 804 may be the result of performing the example method described with respect to FIG. 5 on the same electrochemical system. Heat flux measurements 802 may be obtained when the system is relatively new, or "fresh." In some examples, however, the analysis methods described herein may include assessment of how various components of electrochemical systems react differently after sustained use. That is, while various thermal characteristics of system components may be determined by applying a plurality of signals to the system and measuring the heat response, additional or alternative insights may be determined by modifying the electric state of the system (e.g., charging the system, discharging the system, any combination of charging and discharging, etc.) and re-performing the heat response analysis.

Thus, in order to obtain heat flux measurements 804, the electrical state of the electrochemical system may be modified subsequent to determining the at least one rate at which heat is generated. Thereafter, the plurality of electrical signals are reapplied across the electrochemical system, and at least one second rate at which heat is generated by the electrochemical system in response to the reapplied plurality of electrical signals is determined using the calorimeter (e.g., calorimeter assembly 202). Consequently, determining the at least one thermal characteristic may be further based on the at least one second rate at which heat is generated in response to the reapplied plurality of electrical signals.

As one concrete example, it is evident from FIG. 8 that the heat generated in response to a 10 KHz signal is much higher in the cycled cell compared to the fresh cell. This may indicate that the components associated with the 10 KHz frequency are more prone to failure or overheating. Other example thermal characteristics that may be determined by cycling and reapplying the signals may include loss of usable active material from one or both of the electrodes, electrolyte evaporation, buildup of thermal barrier layers across the porosity of the electrodes that prevent efficient heat distribution across either or both the electrodes.

Figure 9:
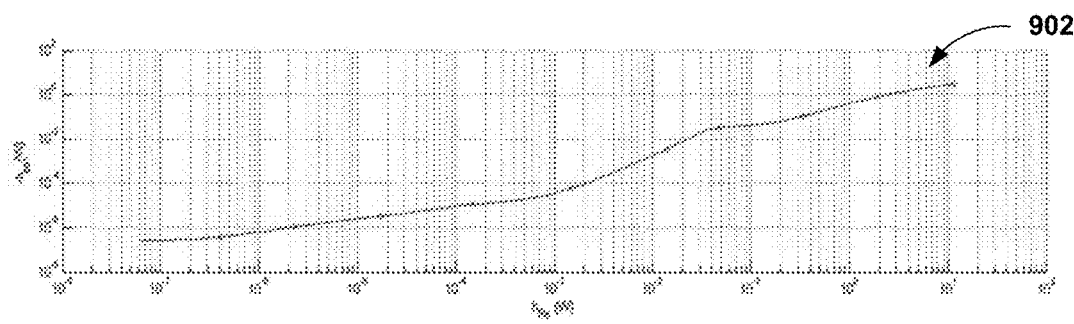
FIG. 9 is a graphical plot illustrating example complex heat flux measurements, in accordance with one or more aspects of the present disclosure.

FIG. 9 is a graphical plot illustrating example complex heat flux measurements 902, in accordance with one or more aspects of the present disclosure. Heat flux measurements 902 may be obtained using the method described with respect to FIG. 5. However, instead of successively applying the electrical signals, a plurality of frequencies may be applied all at once, as a white noise signal. That is, although a plurality of input signals are applied in example of FIG. 5 (e.g., with each having a different frequency), other methods of electrically exciting the electrochemical system may be used in various examples. For instance, using white-noise as the perturbing voltage or current signal may enable the corresponding heat generation rate versus time to be measured and transformed to the frequency domain, to obtain heat generation at different frequencies. The mathematical principle behind transformation of electrical and/or electrochemical impedance data from the time domain into the frequency domain (e.g., using a Fast-Fourier Transform) may be the same for transformation of heat generation data.

Various examples have been described. The foregoing disclosure has been set forth merely as illustration and is not intended to be limiting. Modifications of the disclosed embodiments incorporating the spirit and substance of the device(s) and/or method(s) described herein may occur to persons skilled in the art. These and other examples may be within the scope of the following claims.

What is claimed is:

1. A device comprising:
   a first thermo-electric gauge (TEG);
   a first conductor thermally coupled to the first TEG, first conductor comprising a first surface and a first electrical connection;
   a second conductor comprising a second surface and a second electrical connection, wherein the second surface is facing the first surface, the first surface and the second surface forming a gap;
   a second TEG thermally coupled to the second conductor; and
   an adjustment mechanism attached to the second TEG, operable to modify a size of the gap between the first surface and the second surface, wherein:
   the first conductor further comprises:
      a third surface, different from the first surface,
      a first busbar having a surface that is flush with the third surface, wherein the first electrical connection comprises an end of the first busbar, and wherein the first TEG is thermally coupled to the third surface and to the surface of the first busbar, and
      one or more recesses disposed between at least a portion of the first busbar and the rest of the first conductor; and
   the second conductor further comprises:
      a fourth surface, different from the second surface,
      a second busbar having a surface that is flush with the fourth surface, wherein the second electrical connection comprises an end of the second busbar, and wherein the second TEG is thermally coupled to the fourth surface and to the surface of the second busbar, and
      one or more recesses disposed between at least a portion of the second busbar and the rest of the second conductor.

2. The device of claim 1, wherein the first conductor further comprises one or more recesses that restrict the transfer of thermal energy through the first electrical connection, and wherein the second conductor comprises one or more recesses that restrict the transfer of thermal energy through the second electrical connection.

3. The device of claim 1, further comprising: a housing having a recessed cavity, wherein the first TEG, the first conductor, the second conductor, and the second TEG are located within the recessed cavity of the housing, and wherein at least a portion of the adjustment mechanism is connected to the housing.

4. The device of claim 3, further comprising:
   thermal insulation disposed between an inner surface of the recessed cavity of the housing and at least one of the first TEG, the first conductor, the second conductor, or the second TEG.

5. The device of claim 3, further comprising:
   a lid that is attachable to the housing to enclose the first TEG, the first conductor, the second conductor, and the second TEG within the recessed cavity of the housing, wherein the first TEG is attached to the lid, and wherein the enclosed, recessed cavity is substantially airtight.

6. The device of claim 3, wherein a portion of the adjustment mechanism extends through an opening in the housing, from the recessed cavity, and out of the housing.

7. The device of claim 3, further comprising a thermal plate attached to the adjustment mechanism, the thermal plate having at least one side substantially in contact with a side of the recessed cavity formed by the housing.

8. The device of claim 1, wherein the adjustment mechanism comprises: a threaded adjustment hub; and a corresponding threaded shaft that mechanically interacts with the threaded adjustment hub to modify the size of the gap between the first surface and the second surface.

9. The device of claim 8, further comprising a torque indicator at indicates an amount of torque applied to the threaded adjustment hub.

\* \* \* \* \*